United States Patent [19]

Baird

[11] Patent Number: 4,808,925

[45] Date of Patent: Feb. 28, 1989

[54] THREE MAGNET CASING COLLAR LOCATOR

[75] Inventor: Gary K. Baird, Richmond, Tex.

[73] Assignee: Halliburton Company, Duncan, Okla.

[21] Appl. No.: 122,967

[22] Filed: Nov. 19, 1987

[51] Int. Cl.⁴ .................... G01N 27/72; G01N 27/82; H01F 21/00

[52] U.S. Cl. ...................................... 324/221; 336/110

[58] Field of Search ............... 324/219, 220, 221, 228, 324/346; 336/110

[56] References Cited

U.S. PATENT DOCUMENTS 2,967,994  1/1961  Peterson ............................. 324/221
4,710,741 12/1987  Walkow .............................. 324/221

Primary Examiner—Reinhard J. Eisenzopf
Assistant Examiner—Walter E. Snow
Attorney, Agent, or Firm—William J. Beard

[57] ABSTRACT

For use with casing having flush joint collars, a detection system is set forth which comprises a tool body made of nonmagnetic material and enclosing abutted first, second and third permanent magnets. The magnets are axially aligned, abutted so that opposing poles are in contact with one another, thereby forming a magnetic field from the center magnet which is focused out into the metal of the casing. Separate detection coils spaced along the tool body detect signals induced by variations in magnetic reluctance as the tool traverses the cased well.

6 Claims, 1 Drawing Sheet

THREE MAGNET CASING COLLAR LOCATOR

BACKGROUND OF THE DISCLOSURE

A casing collar locator is a device which finds or locates the collars or basing joints which join a string of well casing together. After a well has been drilled and as part of the completion procedure, the well typically is cased. Casing is assembled by joining individual joints together. They are normally joined with an external collar which threads to a pair of adjacent joints. The extra metal in the large collar is easy to magnetically locate. In recent times, the collar can be avoided by incorporation of a different type of thread construction, namely, omission of the collar for only a pin and box thread connection between adjacent joints. This reduces the mass of metal around the threaded connection. It provides a more uniform wall thickness while reducing the mass of metal around the connection of joints. It is very important to correctly locate the collars or joints so that the depth or location of a tool in the cased well can be determined. Given the fact that casing joints have uniform spacing, the depth of a particular tool suspended in the well can be determined if the casing collars or joints can be correctly counted.

With the advent of the improved threaded joints which reduces the amount of metal at a joint connection, detection is more difficult. Such casing joints are described as having flush collar joints. The adjacent joints are assembled by pin and box construction. This defines a relatively small threaded area which is much more difficult t o locate.

Magnetic casing collar locators of the past have been able to tolerate a wide range of magnetic field dispersion. They have been able to tolerate degraded signal to noise ratios. However, with the advent of the improved flush collar construction, magnetic focusing becomes more crucial. One device used heretofore is described in U.S. Pat. No. 3,434,046. In that disclosure, a common magnetic core for coils is used, the core being well known in the transformer art as a stack of E-shaped laminations which are assembled to form the core. Such a device, however, operates best in a decentralized mode, ideally urged against the wall of the casing. There is frictional drag in such a device. Therefore, its rate of travel in the cased hole is limited. Moreover this particular patent shows centralizing springs which drag against the casing and which ultimately wear out as a result of the dragging action during use. Sensitivity to aberrations in the metal wall is also increased. For instance, if such a detecting structure moves directly over pits, mill scale, etc., the apparatus may very well describe such common metal imperfections as a collar. A centralized tool has the advantage of providing a relatively smaller response to pits because they typically do not fully encircle the casing in the same fashion as does a set of threads. A centralized tool thus is completely surrounded by the threads and perturbations are observed fully around such a tool in the magnetic field which is directed by the improved magnetic system of this invention.

This invention utilizes three permanent magnets which are axially aligned along the tool axis with opposing poles abutted. The magnets are aligned axially as the tool is centered in the casing. The magnets therefore are ideally moved along the centerline axis of the casing. The tool supports the three magnets so that the opposing poles form a focused toroidally shaped magnetic field radiating radially outwardly from the center magnet. Thus, the focused magnetic field has an axial extent that is approximately equal to the length of the center magnet. Ideally, the magnets are identical in magnetic field strength and have identical physical dimensions. This system thus comprises a focused magnetic field system which utilizes permanent magnets to define a toroidally shaped magnetic field sensitive to the threads in the casing wall as a discontinuity in its magnetic circuit. The magnets support detector coils thereon. The preferred embodiment uses two identical detector coils which are spaced along the length of the three serially arranged permanent magnets. As a disturbance or magnetic field anomaly is encountered in the magnetic field, it is observed as a voltage signal induced first in one coil and subsequently as an opposite polarity voltage signaling the other coil. The two coil output voltage signals are provided as inputs to a differential amplifier set up as a summing amplifier so that the two opposing signals cancel one another. This cancels various extraneous signals as will be described, and enables the two summed signals to describe the passage of the focused magnetic field by a set of threads by signal deflection. In other words, a casing collar threaded section is located and identified by means of a strong voltage signal from the summing amplifier which deflects first positive and then negative (or in the reverse sequence depending on the direction of travel of the tool). The voltage signal is then provided to parallel first and second low pass filters. The filtered signal outputs are then provided to a differential amplifier where the two signals are summed. This again helps eliminate noise in the signals and provides a pass band which is defined by the separate cutoff points of the two filters. Useful information is obtained in a specified pass band and can thereafter be additionally amplified and applied to a recorder wherein casing collars can then be counted.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DESCRIPTION OF THE PREFERRED EMBODIMENT

Figure 1:
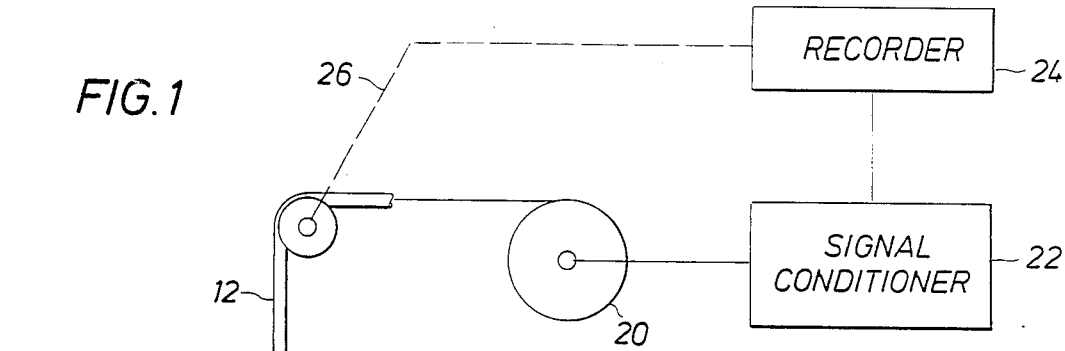
FIG. 1 shows a casing collar locator in accordance with the teachings of the present disclosure suspended in a well bore and adapted to be raised or lowered in the well to locate threaded connections in the surrounding casing.

Attention is first directed to FIG. 1 of the drawings where the numeral 10 identifies a closed housing having the form of a sonde which is lowered in a well borehole on an armored logging cable 12. The cable 12 includes a strength member and electrical conductors as required. The sonde 10 is a sealed, enclosed housing which encloses the apparatus of the present disclosure. It is suspended on the logging cable in a well that is provided wit a casing 14. This casing is provided with flush joints at 16. There is no extra metal at the threaded connection so that it is relatively obscure in terms of forming magnetic disturbances. The cable 12 extends to the surface and passes over a sheave 18. The cable is spooled on a drum 20 and can easily be 25,000 feet long for extremely deep holes. The cable 12 encloses one or more signal conductors which are connected with an output signal conditioner 22. That formats the signal obtained from the sonde 10 and delivers it for recording by a recorder 24. The signal is recorded as a function of depth. Depth in the well is determined by e mechanical or electronic depth measuring apparatus 26 which provides the length of cable in the well so that the recorded data can be correlated with depth.

The sonde 10 is preferably formed of a nonmagnetic material such as aluminum, brass or fiberglass. The nonmagnetic material permits the magnetic lines of flux necessary for operation to extend to the casing 14. The casing 14 is practically always fabricated of ferromagnetic materials and provides a magnetic circuit as will be set forth. An electronic system 30 is included for preparation of the signal for transmission to the surface. The system 30 will be described in detail in FIG. 2 of the drawings. On the interior, a magnetic system is formed of preferably identical permanent magnets which are identified at 32, 34 and 36. The magnets are preferably elongate cylindrical bodies having a length of perhaps two inches to about five inches. All three are preferably identical in size and field strength. They are arranged so that like poles contact. Thus, the south pole of the magnet 32 contacts the south pole of the magnet 34. The contact between the magnets 34 and 36 abuts the north poles in contact with one another. The several magnets are held in this position by internal supportive structure (omitted for sake of clarity) which positions the magnets along the centerline of the sonde 10. In ordinary circumstances, the sonde is intended to hang in the center of the casing and thus the magnets are located at the axis of the casing. The magnets conveniently serve as a support for first and second detection coils identified by the numerals 40 and 44. The coils are preferably identical in turns and spacing so that the magnets have equal sensitivity. They are placed approximately at the junction of the opposing poles. The coils 40 and 44 are thus separated by a distance approximately equal to the length of the permanent magnet 34.

The magnet system shown in FIG. 1 forms a focused, directed magnetic field which is described by the idealized flux lines 48. The field 48 is forced outwardly. This field 48 is flanked by adjacent fields, the upper field being identified by the numeral 50 and the lower field 52. The fields 50 and 52 are important to shaping the field 48. The flux of the field 48 is forced radially outwardly into the magnetic material making up the casing 14; the field 48 reluctance path includes the casing. The casing includes the threaded connection 16. The field 48 from the central magnet is constrained or focused by the adjacent magnetic fields 50 and 52. While the fields 50 and 52 do not form a significant part of the detection circuit, they contribute significantly to reshaping the field 48 whereby the detection circuit responds to the variations in magnetic reluctance caused by the threaded connection 16.

Figure 3:
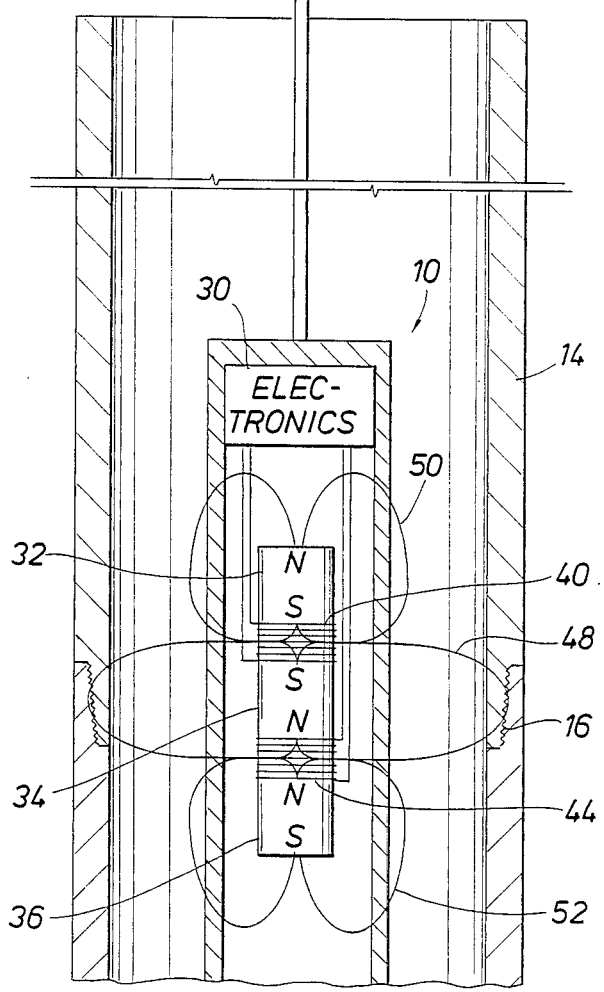
FIG. 3 is a frequency response graph showing separate filters and the summed pass band provided by the filtering system.
Figure 3:
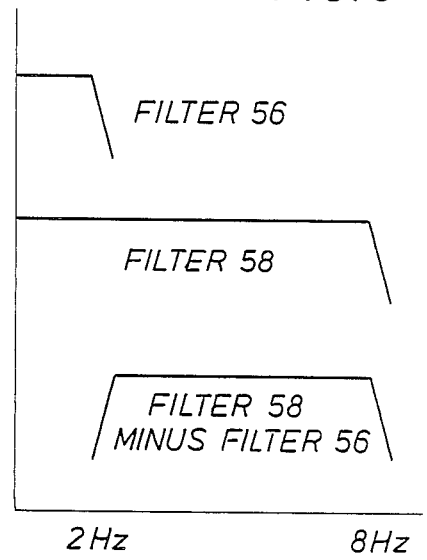
Figure 2:
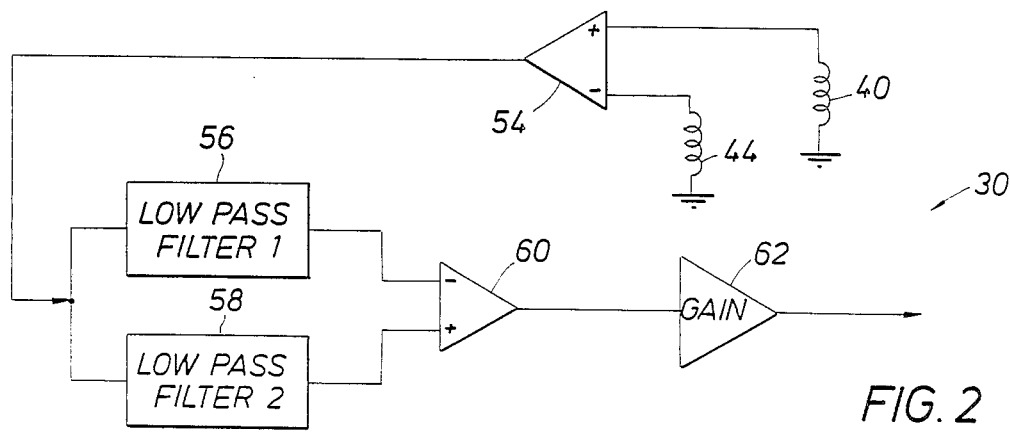
FIG. 2 is a block diagram of the schematic of the electronic system which prepares the signal for transmission to the surface.

Going now to FIG. 2 of the drawings, there it will be observed that the coils 40 and 44 are connected to an amplifier 54. The amplifier 54 is provided with two input terminals and in the preferred embodiment, the signals from the two coils are subtracted from one another so that only differences are amplified. Common signal components arising from movement common to both coils are then canceled. The amplifier 54, although desired for best noise cancellation, is not necessarily required. The coils themselves can be configured such as by placing in parallel or series relationship with signals opposing so that only signal differences are amplified in succeeding circuitry. As an example, signals derived from swaying of the sonde 10 are canceled. Signal cancellation decreases the amount of noise that is supplied through the system and improves the ability to recognize passage of a threaded connection. The amplifier 54 responds to the voltage output signals from the two detection coils. The coils 40 and 44 are passive listening devices wherein changes in magnetic reluctance (during motion) form induced voltages in the two coils. Clearly, a current amplifier system can be used in the alternative. The amplifier 54 forms an output signal which is provided to a first low pass filter identified at 56 and a similar low pass filter 58. The two filters have pass bands described in FIG. 3. The filters 56 and 58 have pass bands which are similar but have different upper cutoff frequencies. The two filters are connected to a summing amplifier 60. It subtracts the two signals so that data within a pass band is then provided to a output amplifier 62. That connects with the conductor which transmits the filtered signal to the surface. The filter 56 has a cutoff frequency represented in FIG. 3 at two hertz. The filter 58 has a cutoff frequency at about eight hertz. As shown in FIG. 3, this defines a pass band which is between about two and eight hertz. More will be noted regarding the end points of the pass band hereinafter.

If a common signal event occurs, the common signal will be canceled by applying the two separate detected signals through the filtering system which is shown in FIG. 2. Moreover, common signal drift is also canceled. Assume for instance that the sonde 10 is being retrieved along the casing at a specified velocity at a depth of 15,000 feet. While there will be a fixed vertical velocity component because the apparatus at the surface retrieves the cable at a fixed rate, there will be another velocity and unwanted component. This results from periodic stretching of the cable. The cable acts as a long spring and the weight suspended at the bottom will oscillate as a result. This error signal will be canceled by this system. Another type of error signal results from sway of the sonde as it is retrieved. As it swings back and forth, the error signal is coupled into both coils, but the error is removed by signal cancellation. Assume also that the casing is badly corroded or pitted on the interior. This will form any number of small disturbances. They are also canceled in some measure by the use of the two coil system. Many other types of small signal disturbances are canceled in this data retrieval system whereby the signals are conditioned as described.

An important feature, however, is the ability of the present apparatus to detect the threads 16. When the threads 16 encounter the field 48, they form a disturbance in that field, namely by changing the magnetic reluctance in the field. This is coupled to first one coil and then the other. The signal is observed in one coil first and then the other coil as the field traverses the threads 16. This forms separate positive and negative signals. The polarity of the coils and the polarity of the various amplifiers may invert the signals but, in general terms, the output signal has both positive and negative going peaks.

The data which is created by the threads 16 is a relatively large signal. Because of the time delay in peak formation in the two formations, the peaks are somewhat symmetrical, both positive going and negative going. Moreover this dynamic signal is in the pass band. The frequency end points of the pass band should be carefully defined relative to the velocity of the tool. If the tool is traveling slowly, the frequency might be lower and hence the pass band should be lower in frequency. In general terms, a pass band of about two hertz to about eight hertz is acceptable for most systems. This will accommodate a range of velocities of the tool. The signal from the system 30 is coupled up the cable and delivered to the surface apparatus. There, it is reported as a function of depth as indicated by the depth measuring apparatus.

Operation of the present apparatus normally involves placing the sonde 10 in the cased hole and spooling the cable in or out at a fixed velocity. To provide a double check, the sonde might be positioned at the mouth of the well and then lowered to the full depth of the hole. As it travels downwardly, data is obtained indicative of collars in the casing string. On retrieval, the same data should be captured as the tool traverses the same collars. This provides two sets of data where the number of collars can be counted and compared to assure that the two counts are equal.

The velocity used for a given circumstance is preferably selected so that the signals are rich in harmonic content to assure that a significant portion of the harmonies fall into the pass band. The incorporation of the pass band system assures in rejection of certain frequency constituents and thereby improves signal to noise ratios.

While the foregoing is directed to the preferred embodiment the scope is determined by the claims which follow.

What is claimed is:

1. A casing collar locator, comprising:
   (a) a non magnetic downhole tool body sized and adapted to be lowered axially in a well borehole;
   (b) three serially positioned permanent bar magnets carried interiorly of said body and abutting at opposing poles wherein the center magnet forms a magnetic field directed outwardly therefrom and the magnetic field is focused radially outwardly by the remaining two magnets to magnetically interact with tubular member threaded joints in the well borehole; and
   (c) detection coil means wound over said magnets and located at the juncture of said opposing poles of said magnets to detect changing magnetic field signals from the threaded joints coupled thereto by the focused magnetic field.

2. The apparatus of claim 1 wherein said three permanent bar magnets are each approximately two inches to five inches in length.

3. The apparatus of claim 2 wherein said detection coil means comprises first and second separate coils having equal sensitivity, and said coils are spaced apart so that the detected magnetic signals from the threaded joints, during use of said casing collar locator, are formed at different times from a given threaded joint.

4. The apparatus of claim 3 including an output circuit which comprises:
   (a) band pass filter means for rejecting certain frequencies and passing selected frequencies within a pass band; and
   (b) amplifying means connected to said filter means for providing an output signal from said detection coil means.

5. The apparatus of claim 4 wherein said band pass filter means includes first and second low pass filters having different high frequency cutoffs, summing means provided with the signals therefrom for subtracting signals so that a pass band is defined in the signals, and rejected signals include those signals ranging from minimal frequency up to the specified low end cutoff of the pass band.

6. The apparatus of claim 5 wherein said detection coil means comprises first and second separate similarly constructed detection coils spaced along the length of said tool body for forming separate output signals and wherein circuit means subtracts said signals from one another to obtain a difference signal to thereby reduce signal noise.

* * * * *